United States Patent [19]

Comera et al.

[11] Patent Number: 5,394,828
[45] Date of Patent: Mar. 7, 1995

[54] APPARATUS FOR THE SOLIDIFICATION OF A DOPED ELECTRICITY CONDUCTING MATERIAL AND THE CONTINUOUS CHECKING OF ITS DOPANT CONTENT

[75] Inventors: Jean Comera, Gieres; Jean-Jacques Favier, Grenoble; André Rouzaud, Seyssinet, all of France

[73] Assignees: Commissariat a L'Energie Atomique; Centre National D'Etudes Spatiales, France

[21] Appl. No.: 990,048

[22] Filed: Dec. 14, 1992

[30] Foreign Application Priority Data

Dec. 23, 1991 [FR] France .................................. 91 15995

[51] Int. Cl.⁶ .................................................. C30B 13/16
[52] U.S. Cl. ............................................ 117/208; 117/13; 117/19; 117/201
[58] Field of Search ..................... 156/601, 605, 616.3, 156/616.4; 422/245; 117/13, 19, 34, 49, 81, 83, 201, 222

[56] References Cited

U.S. PATENT DOCUMENTS

| | | | |
|---|---|---|---|
| 3,119,778 | 1/1964 | Hamilton | 156/605 |
| 3,139,653 | 7/1964 | Orem | 156/616.3 |
| 4,197,273 | 4/1980 | Dusserg et al. | 156/601 |
| 4,600,564 | 7/1986 | Wissalde et al. | 156/601 |
| 4,797,174 | 1/1989 | Comera et al. | 156/616.1 |
| 5,047,113 | 9/1991 | Ostrogorsky | 156/616.3 |

FOREIGN PATENT DOCUMENTS

| | | | |
|---|---|---|---|
| 2597884 | 4/1986 | France | C30B 15/00 |
| 1798222 | 9/1968 | Germany | |
| 222046A | 5/1985 | Germany | C30B 13/28 |

OTHER PUBLICATIONS

Metallurigicial Transactions, vol. 22A, Jun. 1991 pp. 1259–1270, "Growth Kinetics of Solid–Liquid Ga Interfaces: Part I. Experimental" by: S. D. Peteves et al.
Inspect Database, Institute of Electrical Engineers, London GS, S. D. Peteves et al: "A Technique for in–situ Dectection (Abstract) of Growth Dislocations" Accession No. A8703241 & Materials Research Society Symposia Proceedings, vol. 53, 1986, Pittsburgh, US, pp. 323–328.

*Primary Examiner*—R. Bruce Breneman
*Assistant Examiner*—Felisa Garrett
*Attorney, Agent, or Firm*—Hayes, Soloway, Hennessey, Grossman & Hage

[57] ABSTRACT

An apparatus for use in solidification of a doped electrically conducting material and for use in monitoring said solidification is provided. The apparatus includes a first forming means for forming a liquid of undoped material in thermodynamic equilibrium with a solid of the undoped material, and a second forming means for forming a liquid of doped material in thermodynamic equilibrium with a solid of the doped material. Solidification of the conducting material occurs at a solidification interface between the doped liquid and the doped solid in the second forming means. In one preferred embodiment, the apparatus comprises a conductive bridge for short-circuiting the liquids.

11 Claims, 2 Drawing Sheets

APPARATUS FOR THE SOLIDIFICATION OF A DOPED ELECTRICITY CONDUCTING MATERIAL AND THE CONTINUOUS CHECKING OF ITS DOPANT CONTENT

BACKGROUND OF THE INVENTION

1. Field of the Invention

The present invention relates to an apparatus for the solidification of a doped electrically conducting material and for continuously monitoring the dopant content of the material.

The invention is applicable in crystallogenesis for any growth of a doped inorganic, semiconductive or conductive monocrystal. Conductive materials are more particularly metallic materials.

The apparatus according to the invention is also applicable to metal alloys, e.g., to superalloys based on Ni, Cu or Zn.

The dopant can be an impurity introduced into the crystal (of phosphorus or boron in a silicon crystal, gallium in a germanium crystal, iron in a GaAs crystal, etc.) or a substitution element (e.g., indium in a $Ga_{1-x}In_xSb$ crystal with $0 < x \leq 1$, mercury in a $Cd_{1-y}Hg_yTe$ crystal with $0 < y \leq 1$). Moreover, the dopant can represent 0.01 to 99.99% by weight of the crystal.

The invention is also applicable e.g., in metallurgical fields to the production of any alloy whose properties (mechanical, thermal and electrical) are dependent on the fine structure of said alloy and in the fields of microelectronics, integrated optics, crystal lasers, etc.

DESCRIPTION OF THE RELATED ART

Crystalline growth from a molten bath is the most widely used method for producing high quality semiconductor or metallic crystals.

The most sought-after properties in such crystals are crystalline or structural quality and composition homogeneity. The most widely used crystalline growth methods are Czochralski pulling, zone melting, floating zone or the horizontal or vertical Bridgmann or Stockbarger methods.

More specifically, the invention relates to the solidification of a monocrystal according to the Bridgmann or Stockbarger methods, for production of crystals both on earth and in space.

At present, only one method makes it possible to continuously measure opaque material (metal semiconductor) composition of a solid during its production, without disturbing its growth. This method is described in FR-A-2 597 884 and U.S. Pat. No. 4,797,174.

The process described in the above documents allows a continuous measurement of the chemical quality of the crystal formed. Thus, it is possible to act retroactively on the fault causes in the crystal and in this way obtain a solid with improved characteristics. This process is based on the measurement of the temperature difference between a liquid/solid mobile interface and the temperature of a liquid/solid fixed interface of the same alloy having a clearly determined composition.

This type of measurement requires a complicated apparatus, whose applications are limited both on earth and in space. In particular, said apparatus has two juxtaposed furnaces and two cooling systems so that the apparatus has large overall dimensions, the electric power consumed is high and consequently the cost thereof is high. In addition, the apparatus suffers from the impossibility of space production, where the energy and power available are limited.

The other, presently known growth processes have no retroaction or continuous checking, and thus, do not permit optimization of the materials formed.

SUMMARY OF THE INVENTION

The invention therefore relates to an apparatus for the solidification of a doped conductive material making it possible to obviate the disadvantages referred to hereinbefore. In particular, said apparatus permits the continuous measurement of the dopant content of the material, whilst having a much simpler practical construction, as well as smaller overall dimensions and a lower cost than in the prior art.

More specifically, the invention relates to an apparatus for the solidification of an electrically conducting material doped by a dopant and for the continuous checking of the dopant content of said material comprising first means for forming a liquid of said undoped material in thermodynamic equilibrium with a solid of said undoped material, second means for forming a liquid of said doped material in thermodynamic equilibrium with a solid of said doped material, means for electrically shortcircuiting the undoped liquid and the doped liquid and means for measuring an electric potential difference between the undoped solid and the doped solid, said potential difference representing the dopant content at the doped solid-doped liquid interface.

The solid material obtained is monocrystal.

The term "electrically conducting material" is understood to mean both a conductive material and a semiconductive material.

The term "dopant" is understood to mean both impurities and a substitution element of one element of the material by another. In addition, "doped" means a dopant concentration which can range between 0.01 and 49.99% by weight of the crystal, the dopant always being the minority phase of the crystal.

For a given pure or doped compound, the equilibrium temperature of the liquid and solid phases is referred to as the fusion temperature and is designated $T_f$.

During the solidification, the solidification front (i.e., the interface separating the liquid from the solid) is in the superfused state. In other words, the temperature of the interface, designated $T_I$, is below the fusion solidification point of the material.

The temperature $T_I$ of the solidification front is therefore equal to the temperature $T_f - \Delta T$, in which $\Delta T$ represents the superfusion. The superfusion of a pure compound, designated $\Delta T_p$, is very small compared with that of the doped compound, designated $\Delta T_d$. In particular, $\Delta T_d$ is well above $\Delta T_p$ (generally 10 to $10^6$ times higher as a function of the concentration, velocity, etc.) $\Delta T_p$ being close to 0.

According to a preferred embodiment, two separate crucibles are provided for respectively receiving the doped material and the undoped material. Thus, the first means comprises a first elongated crucible for receiving the undoped material, first heating means for heating a first part of said first crucible and for forming therein said undoped liquid and first cooling means for cooling a second part of said first crucible and forming therein said undoped solid and the second means comprises a second elongated crucible for receiving the doped material, second heating means for heating a first part of said crucible and forming therein said doped liquid and second cooling means for cooling a second part of said second crucible and for forming therein said doped solid.

In an apparatus where the doped and undoped materials are subject to a relative displacement with respect to the heating means, the superfusion $\Delta T_p$ of the pure compound is of a kinetic nature and that $\Delta T_d$ of the doped compound is both of a chemical and a kinetic nature.

It can be demonstrated that if v is the Seebeck thermoelectric coefficient at the liquid-solid interface, the potential difference $\Delta V$ between the doped solid and the undoped solid satisfies the equation (1):

$$\Delta V = v \times \Delta T + C_1, \qquad (1)$$

in which $C_1$ is a constant which is a function of the difference of the thermoelectric coefficients of the pure and doped solids, the difference of the thermoelectric coefficients of the pure and doped liquids; of the temperatures of the two electric contacts with the solid and the two electric contacts with the liquid of the measuring means.

Equation (1) applies, provided that the temperatures of the doped solid and the undoped solid are known or equal and that the thermoelectric coefficients of the solid and the liquid vary very slightly with the dopant content.

It is also possible to demonstrate that the superfusion T is directly linked with the dopant concentration C at the doped liquid/doped solid interface. Thus, $\Delta V$ makes it possible to continuously measure the dopant content of the crystal being formed and to react, if necessary, during the growth on the solidification parameters such as e.g., the heating temperature of the liquid and the cooling temperature of the solid, the relative displacement rates of the materials with respect to the heating and cooling systems, so as to adapt the dopant concentration to the needs of the user.

Therefore, the process according to the invention makes it possible to obtain a solid, in which the dopant profile, as a function of the growth direction, is adapted to the needs of the user. Thus, it makes it possible to avoid the irregularities causes by accidental variations in the solidification conditions and therefore obtain better quality products than those of the prior art.

The principle of the measurement used in the invention differs from that used in FR-A-2 597 884 and U.S. Pat. No. 4,797,174. In particular, it is based on the use of two mobile interfaces, one relative to the doped compound and the other relative to the pure compound (or undoped compound). This makes it possible to obtain a certain number of advantages.

In particular, the reference temperature $T_f$ permitting the measurement of the superfusion dT is here a physical constant, because it corresponds to the melting temperature of the pure compound. This eliminates a cause of error existing in the prior art, which is the uncontrolled variation of the reference temperature. Thus, the latter is dependent on convective movements close to the reference interface (i.e., of the pure substance).

Moreover, the apparatus according to the invention is much simpler than that of the prior art. In particular, the heating means of the crucibles can consist of a single furnace. In the same way, the cooling means for the doped and undoped materials can consist of a single cooling system.

Thus, the thermal means (furnace, cooling system, device for supplying energy to the furnace and to the cooling system) as well as the regulating and control electronics are twice as small and less complicated than the prior art. Moreover, the thermal energy and maximum power required are twice as small as in the prior art, everything else being considered equal.

Moreover, the length of the apparatus and its weight are reduced by half compared with the prior art. Thus, the apparatus according to the invention is perfectly adapted to a space application, where the energy, maximum power, weight and overall dimensions are limited.

Advantageous, the measurement point for the potential difference in the doped solid and undoped solid are very close, which facilitates the maintaining thereof at the same temperature.

The apparatus according to the invention is of the Bridgmann or Stockbarger type having a simple modification of the crucible.

BRIEF DESCRIPTION OF THE DRAWINGS

The invention is described in greater detail hereinafter relative to the non-limiting embodiments and with reference to the attached drawings, wherein.

DETAILED DESCRIPTION OF THE PREFERRED EMBODIMENTS

Figure 1:
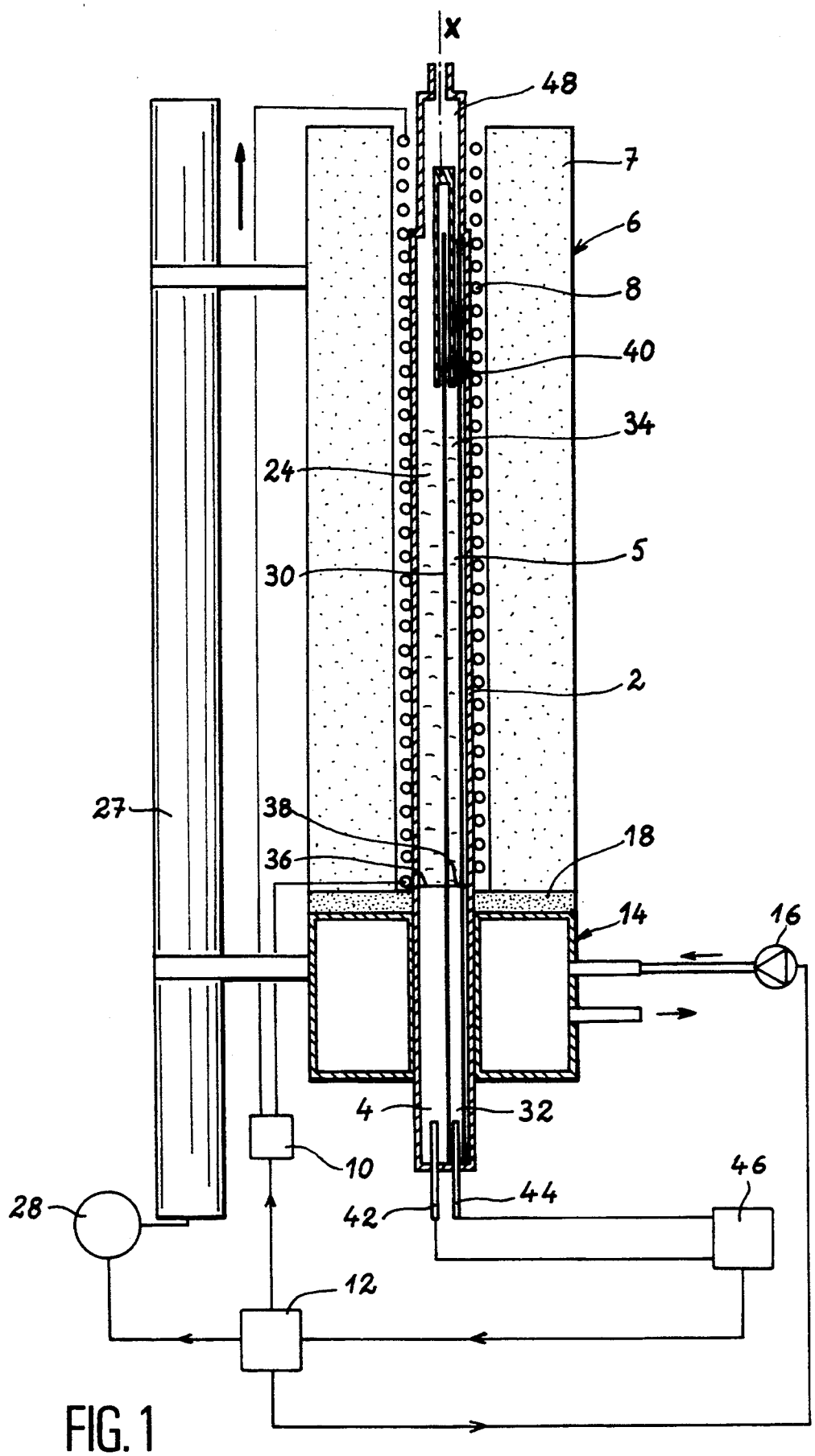
FIG. 1 is a diagram of the appartus according to the invention for a Bridgmann-type vertical solidification.

As in any vertical Bridgmann or Stockbarger apparatus, the apparatus shown in FIG. 1 has a cylindrical crucible 2 with a diameter smaller than its height and which is intended to contain the doped crystal 4 to be produced, X representing the longitudinal axis of the crucible 2.

This apparatus also has a furnace 6 having an axial symmetry and which is equipped with heating resistors 8 (e.g., with a heating power of 500 W) supplied with current by a d.c. power supply 10. The power supply 10 is controlled by a microcomputer-type processing circuit 12.

An electrically and thermally insulating sleeve 7 surrounds the heating elements 8. The appartus also has a cooling system 14 of the water circulation type, placed below the furnace 6 and in the extension thereof. The water circulation system 14 is equipped with an electrovalve 16, also controlled by the processing device 12.

In order to bring about a good separation of the cooling zone and the heating zone, a thermally insulating ring 18 is provided between the furnace 6 and the cooling system 14.

Figure 2:
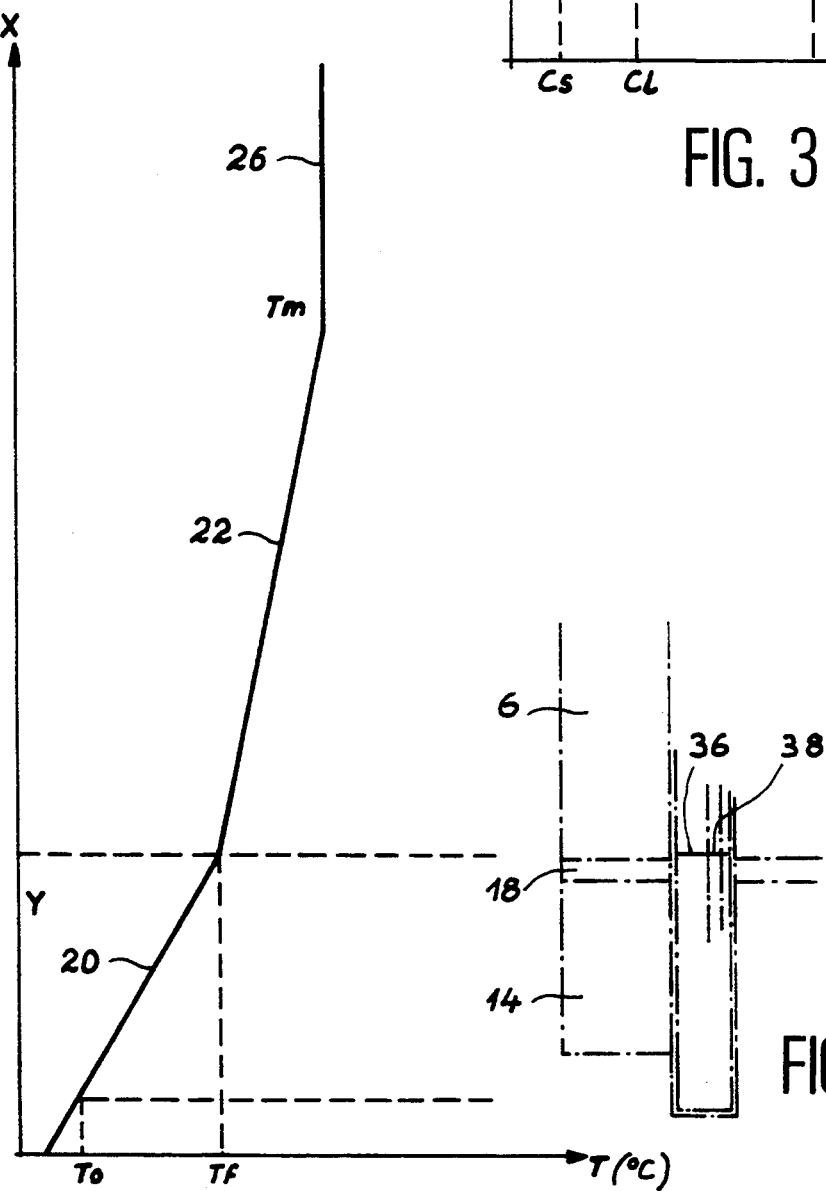
FIG. 2 is a graph showing the longtitudinal temperature profile within the apparatus of FIG. 1.

The furnace 6, insulating ring 18 and cooling system 14 according to the invention makes it possible to obtain a longtitudinal temperature gradient along the axis X o symmetry of the crucible 2, such as is shown in FIG. 2.

The temperature profile of FIG. 2 has a lower part 20 corresponding to a regular increase in the temperature of the doped solid material 4. In said part 20, the temperature passes from the cooling point $T_o$ to the fusion point $T_f$. The temperature $T_o$ is close to 20° C. (or ambient temperature).

The profile of FIG. 2 also has an intermediate part 22 corresponding to a regular temperature of FIG. 2 also has an intermediate part 22 corresponding to a regular temperature rise from the fusion point $T_f$ and then arrives at the maximum heating temperature $T_m$ to which the material is exposed. $T_m$ exceeds the fusion temperature and makes it possible to obtain a doped liquid 24 in thermodynamic equilibrium with the doped solid 4 to be produced. This temperature $T_m$ is maintained over the entire upper part of the furnace, as is illustrated by the vertical part 26 of the curve 2.

The assembly formed by the cooling system 14, insulating ring 18 and furnace 6 is integral with a support 27 equipped with the guidance rails and a motor 28 permitting a translation along the axis X of the assembly 14-18-6, the crucible 2 remaining fixed. The starting up of the motor 28 is also controlled by the microcomputer 12.

According to the invention, there is also a second cylindrical crucible 30 located within the crucible 2 having a diameter smaller than that of the crucible 2. The crucible 30 is in the form of a tube oriented along the axis X of symmetry of the crucible 2 and is integral with the latter. The internal crucible 30 is filled with a compound identical to that to be produced, but which is free from dopant.

The furnace-insulating ring-cooling system assembly makes it possible to obtain doped solid 4 in thermodynamic equilibrium with its doped liquid 20, as well as the obtaining of a pure solid 32 in thermodynamic equilibrium with its undoped liquid 34. References 36 and 38 respectively indicate the doped solid/doped liquid interface and the undoped solid/undoped liquid interface.

In the case of very small dopant concentration, said two interfaces 36 and 38 have very similar dimensions, because the fusion temperatures of the pure or undoped compound and the doped compound differ only slightly.

As solidification is brought about by displacing the furnace-ring-cooling system assembly with respect to the crucibles 2 and 30, the two solid/liquid interfaces 36 and 38 advance simultaneously up to the complete solidification of the pure and doped compounds.

According to the invention and throughout the solidification, the doped and undoped liquids 24, 34 respectively are electrically short-circuited by a hairpin-shaped conductive bridge 40, whereof each branch is immersed in a liquid. The bridge 40 is made from a material which is insoluble in said liquids and chemically inert with respect to said liquids. The doped solid 4 and the undoped solid 32 are provided with an electric contact 42, 44 respectively. These electric contacts are more particularly located in the coldest area of said solids, i.e., at their lower end.

A system 46 makes it possible to measure the potential difference appearing between the electric contacts 42 and 44. The electrical signal supplied by said measuring system 46 is supplied to the microcomputer 12 which, as a function of the measured potential difference, modifies or does not modify the speed of movement of the furnace-ring-cooling system assembly, via the motor 28, the supply voltage of the heating elements 8 of the furnace, via the electric power supply 10, or the flow rate of the cooling liquid, via the opening and closing of the electrovalve 16, in order to modify the temperature profile of the system.

An enclosure 48 fitted at the top of the external crucible 2 makes it possible, if necessary, to place under a vacuum the crucibles, or introduce an inert or reactive gas above the liquids 24 and 34.

The total height of the apparatus according to the invention is roughly twice less than that of the prior art apparatuses. Moreover, the apparatus weights 1.7 times less than the prior art apparatus and consumes 1.8 times less energy than that of the prior art.

Figure 3:
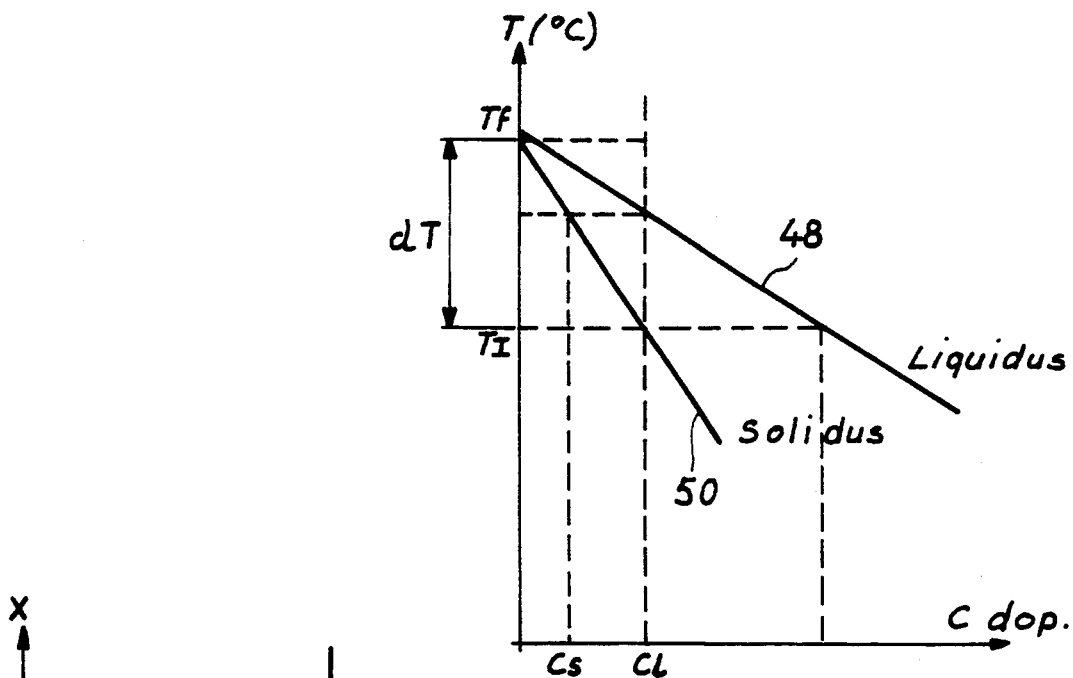
FIG. 3 is a pure compound-dopant phase diagram showing the variations of the fusion temperature $T_f$ as a function of the dopant concentration C in the compound.

If $C_l$ and $C_s$ are used for designating the concentration of the dopant respectively in the doped liquid 24 and the doped solid 4, at the interface 36 and m is the gradient of the liquid curve 48 of the phase diagram of the pure-dopant compound, as shown in FIG. 3 and $K_o$ the thermodynamic distribution coefficient of the dopant in the pure compound, it follows, for systems whose Seebeck coefficient is not dependent on the concentration of the compound, $\Delta V = C_2 + (v_{1l} - v_{sd}) \times m \times C_s/K_o$ with $v_{1d}$ and $v_{sd}$ respectively the Seebeck coefficient of the doped liquid and the Seebeck coefficient of the doped solid and $C_2$ a constant which is a function of the thermoelectric coefficients of the phases present. In other words, $\Delta V = C_3 + C_4 \times C_s$ with $C_3$ and $C_4$ constants dependent on the material to be produced.

Thus, the potential difference dV measured is proportional to the dopant concentration $C_s$ in the doped solid 4 and it is easy to check the latter.

FIG. 3 also shows the solid curve 50 and the superfusion $\Delta T$ between the fusion temperature $T_f$ and the temperature $T_I$ of the doped solid-doped liquid interface 36.

The apparatus according to the invention has been used for the growth of gallium-doped germanium with a concentration of 0.5% by weight.

Thus, the doped solid 4 and the doped liquid 24 are respectively of gallium-doped germanium. The pure solid 32 and the pure liquid 34 are in equilibrium with the latter and are of pure germanium. The electric short-circuit 40 between the two liquids is of tungsten or carbon and the crucibles 2 and 30 are of silica or alumina. The temperatures $T_o$, $T_f$ and $T_m$ are respectively 20° C., 937° C. and 1100° C.

We claim:

1. An apparatus for use in solidification of a doped, electrically conducting material and for use in monitoring said solidification, said apparatus comprising:
   a first forming means for forming a first liquid of undoped material in thermodynamic equilibrium with a first solid of said undoped material;
   a second forming means for forming a second liquid of doped material in thermodynamic equilibrium with a second solid of said doped material, said solidification occuring at a solidification interface between said second liquid and said second solid in said second forming means;
   a short circuiting means for electrically short-circuiting said first liquid and said second liquid; and
   a measuring means for measuring an electric potential difference between the undoped first solid and the doped second solid whereby to permit calculation of the dopant concentration at said interface based upon said electric potential difference.

2. An apparatus according to claim 1, wherein the first forming means comprises a first crucible and the second forming means comprises a second crucible which is separate from the first crucible.

3. An apparatus according to claim 1, wherein the first forming means comprises a first elongated crucible, a first heating means for heating a first part of said first crucible and for forming therein said first liquid and a first cooling means for cooling a second part of said first crucible and forming therein said first solid and wherein the second forming means comprises a second elongated crucible for receiving the doped material, a second heating means for heating a first part of said second crucible and forming therein said second liquid, and a second cooling means for cooling a second part of said second crucible and for forming therein said second solid.

4. An apparatus according to claim 3, wherein the first heating means and the second heating means comprise one and the same furnace.

5. An apparatus according to claim 3, wherein the first cooling means and the second cooling means comprise the same cooling system.

6. An apparatus according to claim 2, wherein the first crucible is located in the second crucible and is integral with said second crucible.

7. An apparatus according to claim 3, and further comprising means for bringing about a relative displacement movement between the first crucible and the first heating means, and the second crucible and the second heating means.

8. An apparatus according to claim 4, wherein the first cooling means and the second cooling means comprise one and the same cooling system.

9. An apparatus according to claim 8, wherein the furnace and the cooling system are positioned one above the other and said apparatus further comprises a thermal insulating means located between the furnace and the cooling system.

10. An apparatus according to claim 1, wherein the means for short-circuiting the liquids comprises a conductor bridge having ends that are respectively immersed in the first liquid and the second liquid, said bridge being chemically inert relative to the first and second liquids and insoluble in said first and second liquids.

11. An apparatus according to claim 1, wherein the measuring means comprises electrical contacts located in the first solid and the second solid at positions that are very close to one another.

* * * * *